United States Patent [19]
Kobayashi et al.

[11] 3,974,030
[45] Aug. 10, 1976

[54] PROCESS FOR PRODUCING YEAST CELLS
[75] Inventors: Tadao Kobayashi, Saga; Akio Yamanoi, Tokyo; Shin-Ichiro Otsuka, Yokohama, all of Japan
[73] Assignee: Ajinomoto Co., Inc., Tokyo, Japan
[22] Filed: June 5, 1975
[21] Appl. No.: 584,152

[30] Foreign Application Priority Data
June 10, 1974 Japan............................ 49-65822

[52] U.S. Cl.................................. 195/27; 195/82; 426/46; 426/60
[51] Int. Cl.² ........................................ C12B 1/00
[58] Field of Search .............. 195/82, 27; 426/41, 426/62, 63, 46, 60

[56] References Cited
UNITED STATES PATENTS
3,769,437   10/1973   Pour-el et al. ........................ 426/11

OTHER PUBLICATIONS
Falanghe et al. "Production of Fungal Mycelial Protein in Submerged Culture of Soybean Whey" Applied Microbiology, vol. 12, 1964, pp. 330–334.

Primary Examiner—A. Louis Monacell
Assistant Examiner—R. B. Penland
Attorney, Agent, or Firm—Hans Berman

[57] ABSTRACT
Certain yeasts are capable of growing in a culture medium containing soybean whey as the main carbon source. The yeast cells have a high protein content, and they are suitable for feed food, and so on.

7 Claims, No Drawings

PROCESS FOR PRODUCING YEAST CELLS

This invention relates to a method of producing yeast cells by culturing yeast in a culture medium containing soybean whey as the major carbon source.

Protein is being extracted from soybeans, and utilized for food and so on. Soybean whey which is the mother liquor obtained after precipitation of soybean protein from the extract was heretofore discharged to waste.

According to this invention, yeasts are cultured on this soybean whey and may be utilized for feed, food and so on.

Soybean whey contains a large amount of stachyose and the only known yeast capable of assimilating soybean whey for growth is a Torula yeast reported by Ryohei Takada ["Shokuryo Kogyo", pp. 283 (1949), published by Kyoritsu Shuppan Co. Japanese Patent Publication No. 23509/1967].

It has now been found that other yeasts are capable of growing in a culture medium containing soybean whey as a main nutrient source, and that their cells have a high protein content.

Yeasts capable of growing well in a culture medium containing soybean whey as a main nutrient source and producing protein-rich cells, are *Debaryomyces vanriji*, *Saccharomyces coreanus*, *Pichia polymorpha*, *Candida cloacae*, and *Candida guilliermondii*. They include:

| | | |
|---|---|---|
| Debaryomyces vanriji | AJ 5058 | FERM P-1865 |
| Saccharomyces coreanus | AJ 4096 | FERM P-2606 |
| Pichia polymorpha | AJ 4148 | FERM P-120 |
| Candida cloacae | AJ 5341 | FERM P-410 |
| Candida guilliermondii | AJ 4532 | FERM P-730 |

The yeasts identified above by FERM P-numbers are available freely from the Fermentation Research Institute, Agency of Industrial Science and Technology, of the Ministry for Industrial Trade and Industry, Chiba, Japan.

The culture media employed for growing cells of these yeasts may consist only of soybean whey as is or in concentrated form. A small added amount of a nitrogen source, such as ammonium chloride, amonium sulfate and urea, is effective in stabilizing the yield of yeast cells.

Soybean whey is produced generally by two processes. In one process, protein is extracted with water or dilute alkali solution from raw soybeans or defatted soybeans, the protein is precipitated from the extract with acid or other protein coagulant, and the precipitate is removed. The remaining mother liquor is called soybean whey. In the other process, whey composition is directly extracted with acidulated water of pH 4–5 or with a protein coagulant solution. The extract is also called soybean whey.

The solid matter in soybean whey may consist, by way of illustration, of:

| | |
|---|---|
| Crude protein | 15 % |
| Saccharides | 53 % |
| sucrose | 25 % |
| stachyose | 19 % |
| others | 9 % |
| Organic acid | 7 % |
| Ash content | 23 % |

The culture medium should be slightly acidic or neutral. The cultivation is carried out aerobically for 4 – 48 hours. The temperature of the culture should be kept at 23° – 40°C, preferably 25° – 34°C. The propagated yeast cells are recovered from the broth by centrifuging or filtering.

Analyses referred to hereinbelow were carried out as follows.

Optical density of the culture broth (O.D.) was determined by measuring absorbancy of a sample, diluted 26 times with water, at 562 nm Crude protein content was calculated as 6.25 times the nitrogen content of dry cell material determined by the Kjeldahl method. Saccharide content was determined by mixing 2.5 ml of a sample with 1.5 ml of 9% hydrochloric acid and 10 ml of water, heating the mixture at 100°C for 90 minutes, neutralizing with sodium hydroxide, and then measuring the glucose content by the method of Fehling Lehmann Schoorl.

The following Examples further illustrate the invention.

EXAMPLE 1

The yeast strains described in Table 1 were cultured on agar slants (1 g/dl yeast extract, 1 g/dl malt extract, 0.2 g/dl glucose, 0.5 g/dl NaCl, 2.2 g/dl agar, pH 6.5) at 31.5°C for 24 hours. 30 ml batches of soybean whey (saccharide concentration 1.1 g/dl) mixed with 0.7 g/dl $NH_4Cl$, 0.1 g/dl $KH_2PO_4$, and 0.05 g/dl $MgSO_4.7H_2O$, adjusted to pH 5.0 were seeded each with one half slant and cultured at 31.5°C for 11 hours with shaking.

Batches of culture medium were each prepared from 150 ml of soybean whey (specific gravity 1.045/25°C) by diluting the whey with two volumes of water, adjusting to pH 5.0, and then sterilizing. Ten per cent of each seed culture was inoculated into respective culture media, and the inoculated media were cultured at 31.5°C for 14 hours with aerating and stirring (1/1 v/v, 1200 r.p.m.).

The amounts of yeast cells, crude protein, and residual saccharide in the cultured broths were measured and the results are listed in Table 1.

The soybean whey employed in this example was a mother liquor produced by extracting defatted soybeans with hot water, precipitating protein by adjusting the pH of the extract to 4.3, and then removing the precipitate.

EXAMPLE 2

A culture medium containing:

| | |
|---|---|
| Stachyose | 1.0 g/dl |
| Yeast extract | 0.1 " |
| Soybean protein hydrolyzate ("Mieki") | 0.5 ml/dl |
| $KH_2PO_4$ | 0.1 g/dl |
| $MgSO_4 . 7H_2O$ | 0.05 " |
| $Fe^{++}, Mn^{++}$ | each 5 ppm |
| $NH_4Cl$ | 0.4 g/dl |
| pH 4.0 | | was prepared. A 50 ml batch was placed in a 500 ml shaking flask and sterilized.

The medium was inoculated with ½ slant of Debaryomyces vanriji AJ 5058 (FERM P-1865) which had previously been cultured on an agar slant (1g/dl yeast extract, 1 g/dl malt extract, 0.5 g/dl NaCl, 2 g/dl agar) at 31°C for 24 hours, and cultured first at 31.5°C for 4 hours with shaking, mixed with 5 g/dl calcium carbonate, and further cultured for 20 hours with shaking.

The residual saccharide concentration in this broth was found to be 0.02 g/dl, i.e., 98% of the stachyose initially present was assimilated during culturing.

EXAMPLE 3

Defatted soybeans were extracted with dilute hydrochloric acid at 20°C for 30 minutes, and 50 ml extract containing 2.40 g/dl saccharides was adjusted to pH 4.0, placed in a 500 ml shaking flask, and sterilized.

The medium was inoculated with ½ slant of Debaryomyces vanriji AJ 5058 (FERM P-1865) which was prepared as described in Example 2, and cultured at 31.5°C for 8 hours with shaking.

Dry cell material in an amount of 1.69 g/dl was obtained. The residual saccharide concentration in the cultured broth was 0.31 g/dl, i.e., the yield based on consumed saccharide was 81%.

Table 1

| Strain | Dry cell material | Crude protein | Residual saccharide |
|---|---|---|---|
| | g/dl | % | g/dl |
| Saccharomyces coreanus AJ 4096 | 0.81 | 60.0 | 0.05 |
| Saccharomyces lactis AJ 5012 | 0.53 | 58.1 | 0.09 |
| Saccharomyces robustus AJ 4067 | 0.52 | 61.3 | 0.07 |
| Debaryomyces vanriji AJ 5058 | 0.90 | 51.3 | 0 |
| Debaryomyces nicotianae AJ 4985 | 0.59 | 42.5 | 0 |
| Pichia polymorpha AJ 4148 | 1.00 | 46.3 | 0.05 |
| Pichia ohmeri AJ 5090 | 0.43 | 46.8 | — |
| Candida cloacae AJ 5341 | 1.05 | 50.6 | 0 |
| Candida guilliermondii AJ 4532 | 1.02 | 40.9 | — |
| Candida utilis AJ 4643 | 0.45 | 61.3 | 0.27 |
| Torulopsis spherica AJ 4399 | 0.48 | 61.3 | 0.09 |

Table 1-continued

| Strain | Dry cell material | Crude protein | Residual saccharide |
|---|---|---|---|
| Torulopsis candida AJ 4363 | 0.91 | 39.4 | 0 |
| Torulopsis fructus AJ 4402 | 0.09 | 44.4 | — |

What is claimed is:

1. A method or producing yeast cells which comprises culturing a yeast belonging to species *Debaryomyces vanriji*, *Saccharomyces coreanus*, *Pichia polymorpha*, *Candida cloacae* or *Candida guilliermondii* in an aqueous culture medium containing soybean whey as a major nutrient source for growth of said yeast until the cells of said yeast propagate in said culture medium, and recovering the propagated cells from said medium, said yeast being *Debaryomyces vanriji* FERM P-1865, *Saccharomyces coreanus* FERM P-2606, *Pichia polymorpha* FERM P-120, *Candida cloacae* FERM P-410 or *Candida guilliermondii* FERM P-730.

2. A method as set forth in claim 1, wherein said yeast is *Debaryomyces vanriji* FERM P-1865.

3. A method as set forth in claim 1, wherein the nutrients in said culture medium include stachyose as a main carbon source, a nitrogen source, inorganic salts and minor organic nutrients.

4. A method as set forth in claim 3, wherein said yeast is *Debaryomyces vanriji* FERM P-1865.

5. A method as set forth in claim 1, wherein said soybean whey is the sole major nutrient source in said culture medium.

6. A method as set forth in claim 1, wherein said soybean whey is the sole major source of assimilable carbon in said culture medium.

7. A method as set forth in claim 1, wherein said soybean whey is an aqueous soybean extract containing organic and inorganic solids, said organic solids mainly consisting of saccharides.

* * * * *